(12) United States Patent
Ido

(10) Patent No.: US 7,596,985 B2
(45) Date of Patent: Oct. 6, 2009

(54) IMPACT TEST APPARATUS

(75) Inventor: Osamu Ido, Hino (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 12/139,732

(22) Filed: Jun. 16, 2008

(65) Prior Publication Data

US 2008/0282767 A1  Nov. 20, 2008

Related U.S. Application Data

(63) Continuation of application No. PCT/JP2005/023172, filed on Dec. 16, 2005.

(51) Int. Cl.
*G01N 3/56* (2006.01)

(52) U.S. Cl. .................. 73/11.01; 73/12.06; 73/12.13

(58) Field of Classification Search ..... 73/12.01–12.14, 73/11.01–11.03; 72/12.01–12.14
See application file for complete search history.

(56) References Cited

U.S. PATENT DOCUMENTS

| | | | |
|---|---|---|---|
| 5,006,799 A * | 4/1991 | Pfanstiehl | 324/230 |
| 5,119,916 A * | 6/1992 | Carmen et al. | 194/210 |
| 5,177,370 A * | 1/1993 | Meister | 307/10.1 |
| 6,053,406 A * | 4/2000 | Litman | 235/449 |
| 7,026,946 B2 * | 4/2006 | Saunders et al. | 340/666 |
| 7,209,844 B2 * | 4/2007 | Merrick et al. | 702/65 |

FOREIGN PATENT DOCUMENTS

| | | |
|---|---|---|
| JP | 52-101484 U | 8/1977 |
| JP | 3-148033 A | 6/1991 |
| JP | 3-287045 A | 12/1991 |
| JP | 52-101484 U | 8/1997 |
| JP | 2003-194690 A | 7/2003 |

OTHER PUBLICATIONS

Notification of Transmittal of Translation of the International Preliminary Report on Patentability (Form PCT/IB/338) of International Application No. PCT/JP2005/023172 mailed Jun. 26, 2008 with Forms PCT/IB/373, PCT/IB/326, and PCT/ISA/237.
International Search Report of PCT/JP2005/023172, date of mailing Mar. 20, 2006.

* cited by examiner

*Primary Examiner*—Max Noori
(74) *Attorney, Agent, or Firm*—Westerman, Hattori, Daniels & Adrian, LLP

(57) ABSTRACT

An impact test apparatus allows a retaining member to retain a test object. The retaining member is attached to an elastic member. When a weight is made to collide against the test object, impact is applied to the test object. The test object is subjected to free oscillation in response to the impact. The elasticity of the elastic member accepts the movement of the retaining member. Damping of the free oscillation of the test object is minimized. The impact test sufficiently reflects the influence of the free oscillation.

2 Claims, 5 Drawing Sheets

IMPACT TEST APPARATUS

BACKGROUND OF THE INVENTION

1. Field of the Invention

The present invention relates to an impact test apparatus allowing a weight to collide against a test object for testing or measuring the strength of the test object, for example.

2. Description of the Prior Art

Solder bumps are employed to bond a large-scale integrated (LSI) circuit package and a printed wiring board. The solder bumps are arranged to establish a so-called ball grid array (BGA), for example. An impact test is executed so as to evaluate the bonding strength of the ball grid array. Four corners of the printed wiring board are fixed to a support for the impact test. A weight is made to collide against the printed wiring board. Subsequently, electric connection is examined between the printed wiring board and the LSI package.

In general, an electronic apparatus such as a mobile phone terminal suffers from free oscillation after the application of impact of a fall. According to an observation by the present inventor, it has been confirmed that the free oscillation has a large influence on the bonding strength. In a conventional impact test, screws are employed to attach the printed wiring board on the support. It is thus impossible to examine the influence of the free oscillation in the impact test.

SUMMARY OF THE INVENTION

It is accordingly an object of the present invention to provide an impact test apparatus enabling to sufficiently reflecting the influence of the free oscillation.

According to a first aspect of the present invention, there is provided an impact test apparatus comprising: a support; an elastic member coupled to the support; a retaining member attached to the elastic member so as to retain a test object; and a weight made to collide against the test object.

The impact test apparatus allows the retaining member to retain the test object. The retaining member is attached to the elastic member. When the weight is made to collide against the test object, impact is applied to the test object. The test object is subjected to free oscillation in response to the impact. The elasticity of the elastic member accepts the movement of the retaining member. Damping of the free oscillation of the test object is minimized. The impact test sufficiently reflects the influence of the free oscillation.

In the impact test apparatus of this type, the allowable distance of relative movement between the retaining member and the test object may be set smaller than that of relative movement between the retaining member and the support. While the retaining member rigidly retains the test object, the elasticity of the elastic member allows the movement of the retaining member. The movement of the test object is thus sufficiently realized. A coil spring may be employed as the elastic member, for example.

According to a second aspect of the present invention, there is provided an impact test apparatus comprising: a support; a first magnet fixed to the support; a second magnet supported on the support for relative movement based on a repulsion between the first magnet and the second magnet; a retaining member attached to the second magnet so as to retain a test object; and a weight made to collide against the test object.

The impact test apparatus allows the retaining member to retain the test object. The retaining member is attached to the second magnet. When the weight is made to collide against the test object, impact is applied to the test object. The test object is subjected to free oscillation in response to the impact. The repulsion between the first and second magnets accepts the movement of the second magnet or retaining member along the support. Damping of the free oscillation of the test object is minimized. The impact test sufficiently reflects the influence of the free oscillation.

In the impact test apparatus of this type, the allowable distance of relative movement between the retaining member and the test object may be set smaller than that of relative movement between the retaining member and the support. While the retaining member rigidly retains the test object, the repulsion between the first and second magnets allows the movement of the retaining member. The movement of the test object is thus sufficiently realized.

BRIEF DESCRIPTION OF THE DRAWINGS

The above and other objects, features and advantages of the present invention will become apparent from the following description of the preferred embodiments in conjunction with the accompanying drawings, wherein.

DESCRIPTION OF THE PREFERRED EMBODIMENTS

Figure 1:
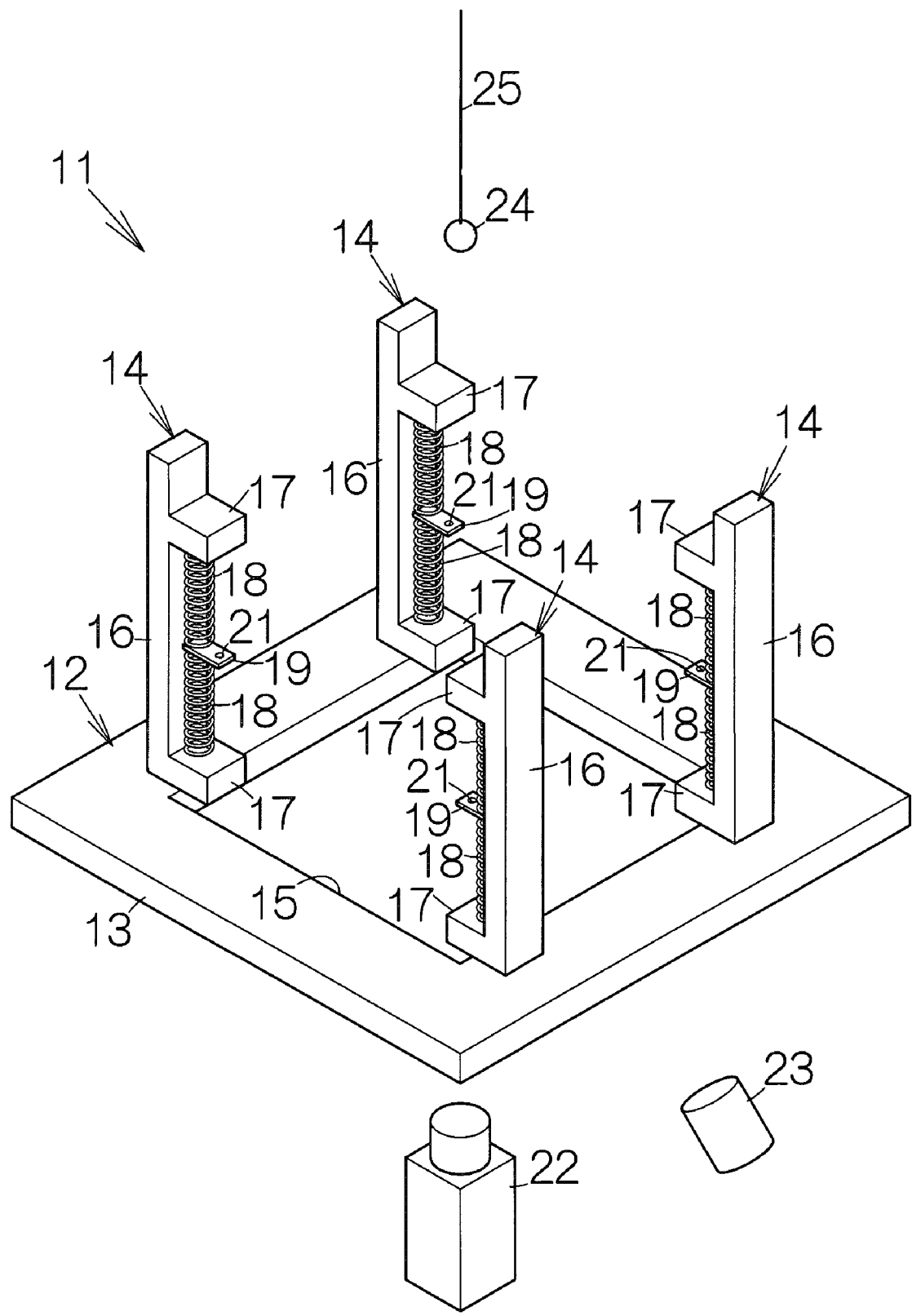
FIG. 1 is a perspective view schematically illustrating an impact test apparatus according to a first embodiment of the present invention.

FIG. 1 schematically illustrates an impact test apparatus 11 according to a first embodiment of the present invention. The impact test apparatus 11 includes a support 12. The support 12 includes a base 13 extending along the horizontal plane, and four support posts 14 standing upright from the base 13, for example. A window opening 15 is defined in the base 13. The base 13 is immobilized on a support table, not shown, for example. The base 13 may be made of a metallic material such as aluminum, for example.

The support posts 14 are fixed to the base 13. The individual support posts 14 include a main elongated body 16 standing upright from the base 13 and a pair of upper and lower protrusions 17, 17 protruding from the main body 16. The upper and lower protrusions 17, 17 are spaced from each other at a predetermined interval in the vertical direction. The upper and lower protrusions 17 may be formed integral with the main body 16. The upper and lower protrusions 17 protrude from the support post 14 in the horizontal direction in parallel with the surface of the base 13. The main body 16 and the protrusions 17 may be made of a metallic material such as aluminum as a one-piece component, for example.

A pair of elastic members or coil springs 18, 18 are arranged in series between the upper and lower protrusions 17, 17 of the individual support posts 14. A retaining member 19 is interposed between the coil springs 18, 18. The coil springs 18 serve to couple the upper and lower protrusions 17 to the retaining member 19. Here, the retaining member 19 is spaced from the side surface of the main body 16 at a predetermined interval.

A threaded through bore 21 is formed in the retaining member 19. The retaining member 19 serves to retain a test object or test sample as described later. A screw may be screwed into the through bore 21 to retain the text sample, for example. The elasticity of the coil springs 18 accepts the vertical movement of the retaining member 19, namely the test sample, along the main body 16.

A high-speed camera 22 and a light source, namely an illuminator 23, are placed at a position below the base 13. The high-speed camera 22 is focused on the test sample placed within the window opening 15. Here, the optical axis of the high-speed camera 22 is aligned with the vertical direction perpendicular to the surface of the base 13. The illuminator 23 is covered with stripes, for example. The illuminator 23 thus serves to project moiré fringes on the test sample placed within the window opening 15. The high-speed camera 22 serves to capture the image of the projected moiré fringes.

A computer apparatus, not shown, is connected to the high-speed camera 22 and the illuminator 23. The captured image is transmitted to the computer apparatus as image data. In the computer apparatus, the image data is analyzed based on the processing of a software program, for example. Various types of data are generated through the analysis as described later.

A weight 24 is set at a position above the base 13. The weight 24 may be hung at the height of 1 [m] approximately from the retaining member 19, for example. A string 25 is employed to hang the weight 24, for example. The weight 24 is made to fall toward the base 13. A steel ball may be employed as the weight 24, for example. The weight of the steel ball may be set at 10 or several dozen grams, approximately, for example. It should be noted that a hammer or a pole may be employed as the weight 24 in place of the steel ball, for example.

A secondary collision prevention mechanism, not shown, is coupled to the weight 24 in a conventional manner. The weight 24 bounces back from the test sample after the collision against the test sample. The secondary collision prevention mechanism allows prevention of a collision of the weight 24 after the bounce of the weight 24. The secondary collision prevention mechanism may be connected to the aforementioned computer apparatus. The computer apparatus may automatically determine conditions such as the fall height and timing of the free fall of the weight 24.

Figure 2:
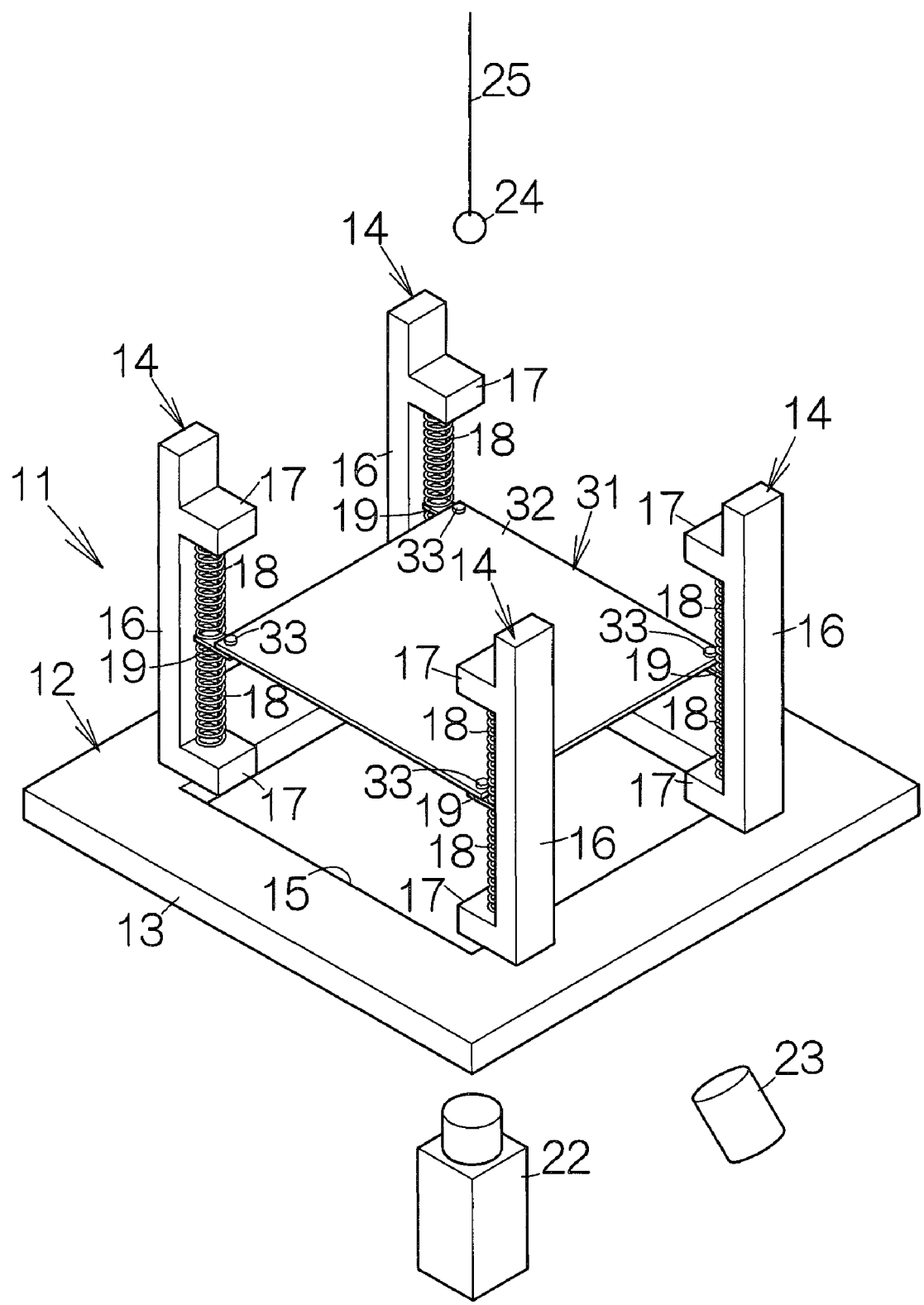
FIG. 2 is a perspective view schematically illustrating the impact test apparatus with a test sample attached.

Now, assume that impact is applied on the test sample. As shown in FIG. 2, a test sample 31 is attached to the impact test apparatus 11. The test sample 31 includes a printed wiring board 32 made of a resin material, for example. Screws 33 are employed to couple the printed wiring board 32 to the individual retaining members 19, for example. The screw 33 is screwed into the threaded through bore 21 of the corresponding retaining member 19. The printed wiring board 32 is in this manner retained on the retaining members 19 along a horizontal plane, for example.

Figure 3:
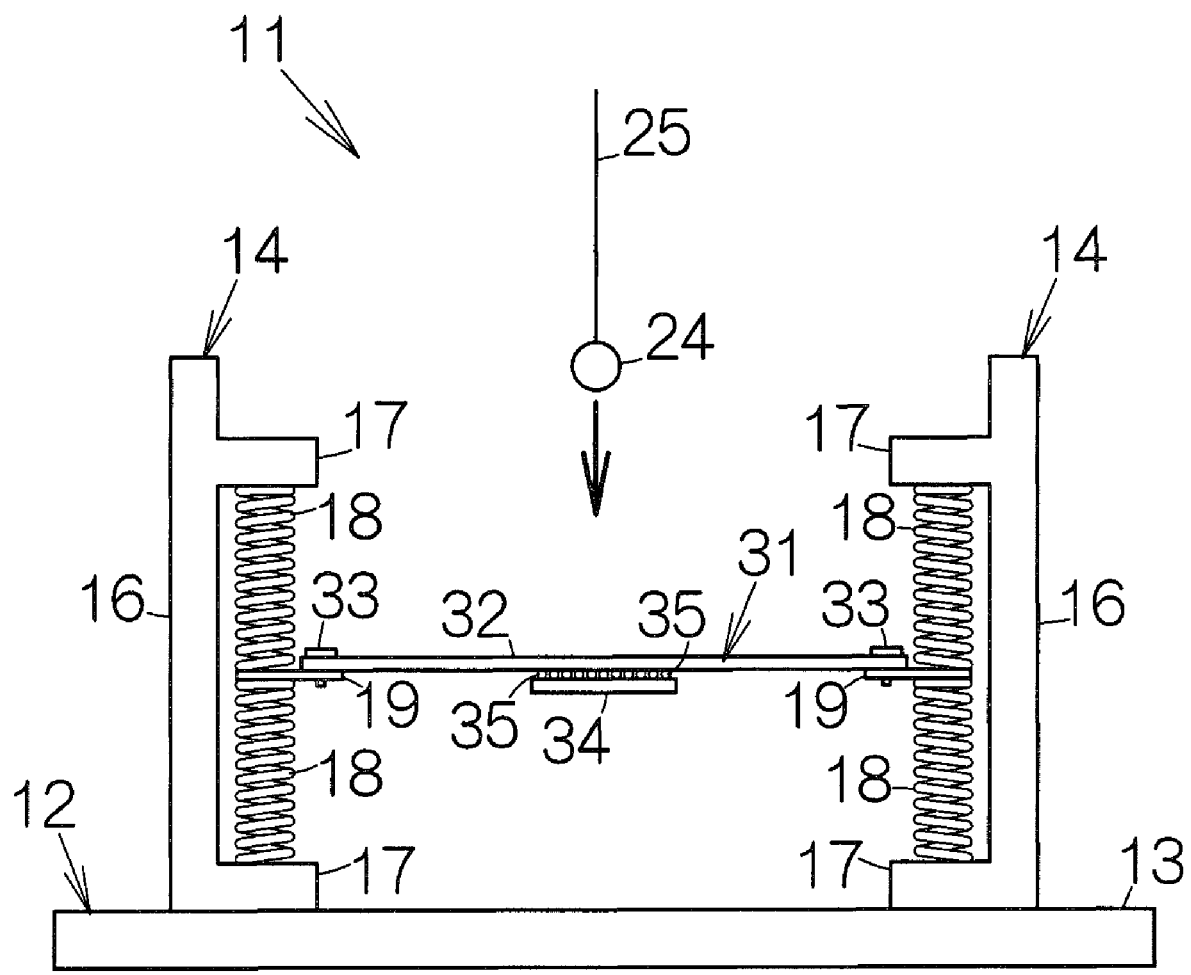
FIG. 3 is a side view of the impact test apparatus schematically illustrating the free fall of an weight to the test sample.

Referring also to FIG. 3, the test sample 31 includes a large-scale integrated circuit (LSI) package 34 mounted on the surface of the printed wiring board 32. Solder balls 35, 35, . . . are employed to bond the LSI package 34 to an electrically-conductive pad, not shown, of the printed wiring board 32. The solder balls 35 are arranged in a lattice pattern, for example. A so-called ball grid array (BGA) is established based on the solder balls 35.

In the impact test apparatus 11, the screws 33 are employed to fix the test sample 31 to the retaining members 19. The coil springs 18 serve to couple the retaining member 19 to the corresponding support post 14. The allowable distance of relative movement between the test sample 31 and the retaining member 19 is thus set significantly smaller than that of relative movement between the retaining member 19 and the support post 14.

As is apparent from FIG. 3, when the test sample 31 is attached to the impact test apparatus 11, the surface of the printed wiring board 32 is positioned at a location opposed to the window opening 15 of the base 13. The high-speed camera 22 is thus focused on the LSI package 34 and the surface of the printed wiring board 32. The illuminator 23 serves to generate moiré fringes on the surfaces of the LSI package 34 and the printed wiring board 32. The weight 24 is set at a position directly above the LSI package 34, for example.

The weight 24 is then subjected to a free fall to the upward back surface of the printed wiring board 32. The secondary collision prevention mechanism allows the weight 24 to collide against the back surface of the printed wiring board 32 only once. The impact of the collision leads to generation of distortion in the printed wiring board 32 and the LSI package 34. The test sample 31 is subjected to free oscillation by the effect of the distortion. The LSI package 34 and the printed wiring board 32 resonate at a specific frequency.

The test sample 31 is rigidly fixed on the retaining members 19 with the screws 33. The elasticity of the coil springs 18 thus allows the test sample 31 to move in the vertical direction along the support post 14 along with the retaining members 19. Such a vertical movement serves to maintain the free oscillation of the test sample 31. The elasticity of the coil springs 18 makes the free oscillation damps as time elapses. After a predetermined duration has elapsed, the printed wiring board 32 rests.

The high-speed camera 22 captures an image of the moiré fringes on the surfaces of the LSI package 32 and the printed wiring board 32. The captured image is transmitted to the computer apparatus as image data, for example. The image data is sequentially generated at predetermined time intervals, for example. The computer apparatus operates to specify temporal changes on the deformation of the moiré fringes. The deformation of the LSI package 34 and the printed wiring board 32 is in this manner observed. Simultaneously, electric connection is examined between the LSI package 34 and the printed wiring board 32. Damage such as a crack or a fracture to the solder balls 35 is determined based on the examination of the electric connection.

The impact test apparatus 11 may accept repetition of the impact test. The same weight 24 may be made to repeatedly collide against the test sample 31, for example. The deformation of the test sample 31 and the damage to the solder balls 35 may be examined every time when the weight 24 is made to collide. The bonding strength is in this manner evaluated between the LSI package 34 and the printed wiring board 32. The service life of the bonding between the LSI package 34 and the printed wiring board 32 is calculated based on the bonding strength, for example.

The weights 24 having different masses may be employed in the impact test in the impact test apparatus 11. In this case, test samples of the identical structure may be prepared for the weights 24, respectively. The influence of the free oscillation is in this manner evaluated for the individual impact having different magnitudes. The weight 24 of a sole kind may be made to collide against test samples 31 having different structures. In this case, the test samples 31 may have solder balls made of materials having different compositions, for example. The influence of the free oscillation is in this manner evaluated for the solder balls made of materials having different composition.

The impact test apparatus 11 allows the vertical movement of the test sample 31 based on the elasticity of the coil springs 18. Specifically, the impact makes the test sample 31 move in the vertical direction. The test sample 31 is thus allowed to receive an impact almost identical to that of the actual fall. In this case, the printed wiring board 32 and the LSI package 34 are subjected to a free oscillation. The elasticity of the coil springs 18 contributes to minimization of damping of the free oscillation. The impact test sufficiently reflects the influence of the free oscillation after the collision.

In addition, as long as conditions, such as the spring constant and length of the coil springs 18 and the mass and fall height of the weight 24, are maintained, it is possible to repeatedly apply the uniform impact test to the test sample 31 under the same conditions. The bonding strength of the solder balls 35 is accurately evaluated, for example. On the other hand, a conventional impact test employs a free fall of the test sample 31, for example. This conventional impact test has a significantly low repeatability. The impact test apparatus 11 according to the present invention contributes to a reduced time required for the impact test.

Furthermore, the computer apparatus is allowed to obtain various types of data, such as deformation amount of the LSI package 34 and the printed wiring board 32, a period of oscillation, a duration of oscillation, and the like, with a higher accuracy, based on the repetition of the aforementioned impact test. Parameters utilized in a numeric simulation for an impact test are derived based on the obtained data, for example. Simultaneously, the damping coefficient of oscillation can be presumed for each component of an electronic apparatus, for example.

Figure 4:
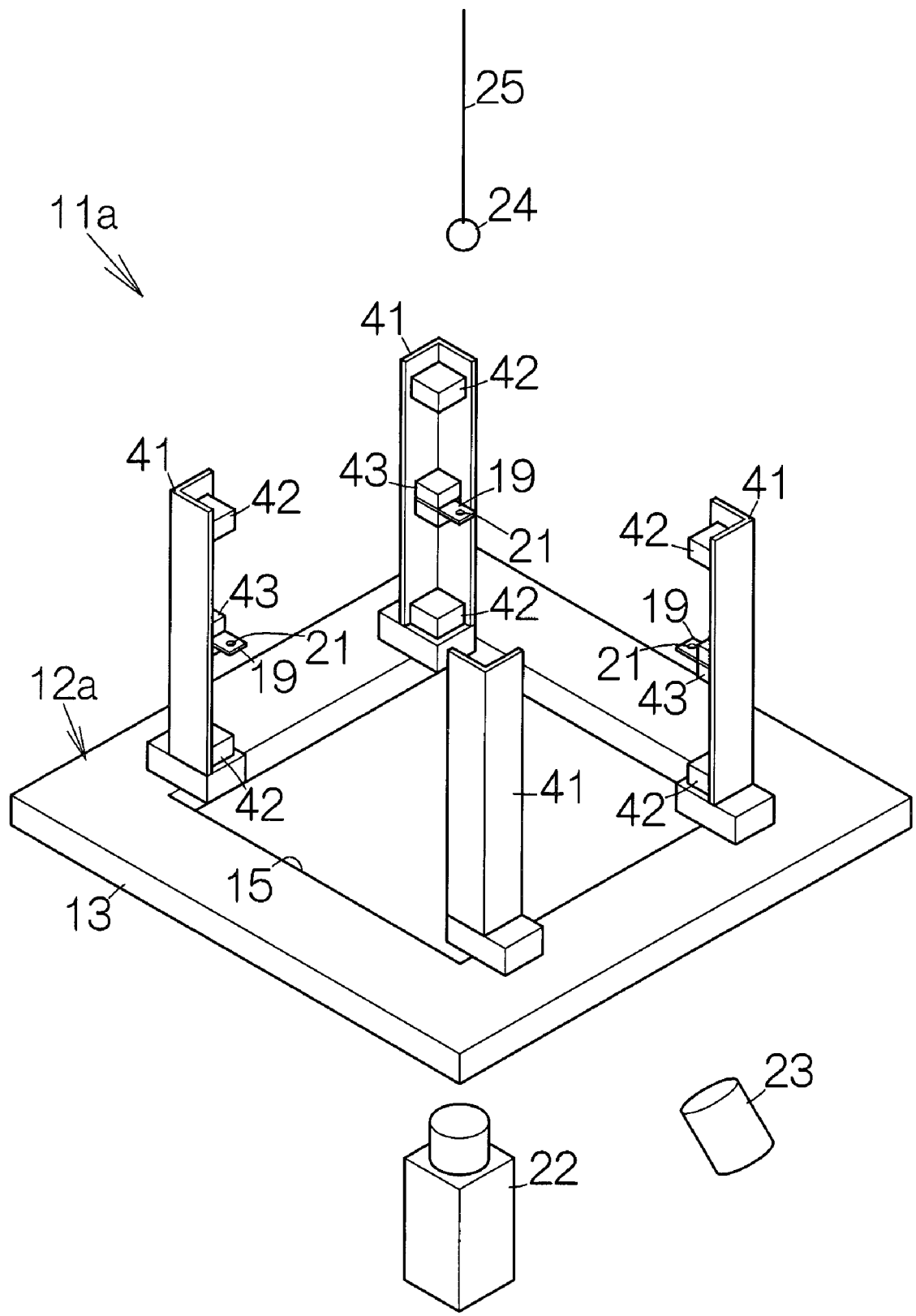
FIG. 4 is a perspective view schematically illustrating an impact test apparatus according to a second embodiment of the present invention.

FIG. 4 schematically illustrates an impact test apparatus 11a according to a second embodiment of the present invention. The impact test apparatus 11a utilizes a support 12a including four support posts 41 fixed to the base 13, for example. The individual support posts 41 have an L-shaped cross-section. The inner surfaces of the four support posts 41, 41, . . . are positioned to contour a space of a parallelepiped standing upright on the base 13. The support posts 41 may be made of a metallic material such as aluminum, for example.

A pair of upper and lower first magnets 42, 42 are fixed to the inner surfaces of the individual support posts 41. An adhesive or a screw may be employed to fix the first magnets 42, for example. The upper and lower first magnets 42, 42 are spaced from each other at a predetermined interval in the vertical direction. A second magnet 43 is placed in a space between the upper and lower first magnets 42, 42. The aforementioned retaining member 19 is attached to the second magnet 43. The retaining member 19 may be held between a pair of magnets, for example.

The first and second magnets 42, 43 may be a permanent magnet, for example. The first and second magnets 42, 43 locate the same poles in opposed relation. The second magnet 43 is thus allowed to float between the upper and lower first magnets 42, 42. The repulsion between the first magnets 42 and the second magnet 43 accepts the vertical movement of the second magnet 43, namely the retaining member 19, along the support post 41. Like reference numerals are attached to the structure or components equivalent to those of the aforementioned first embodiment.

Figure 5:
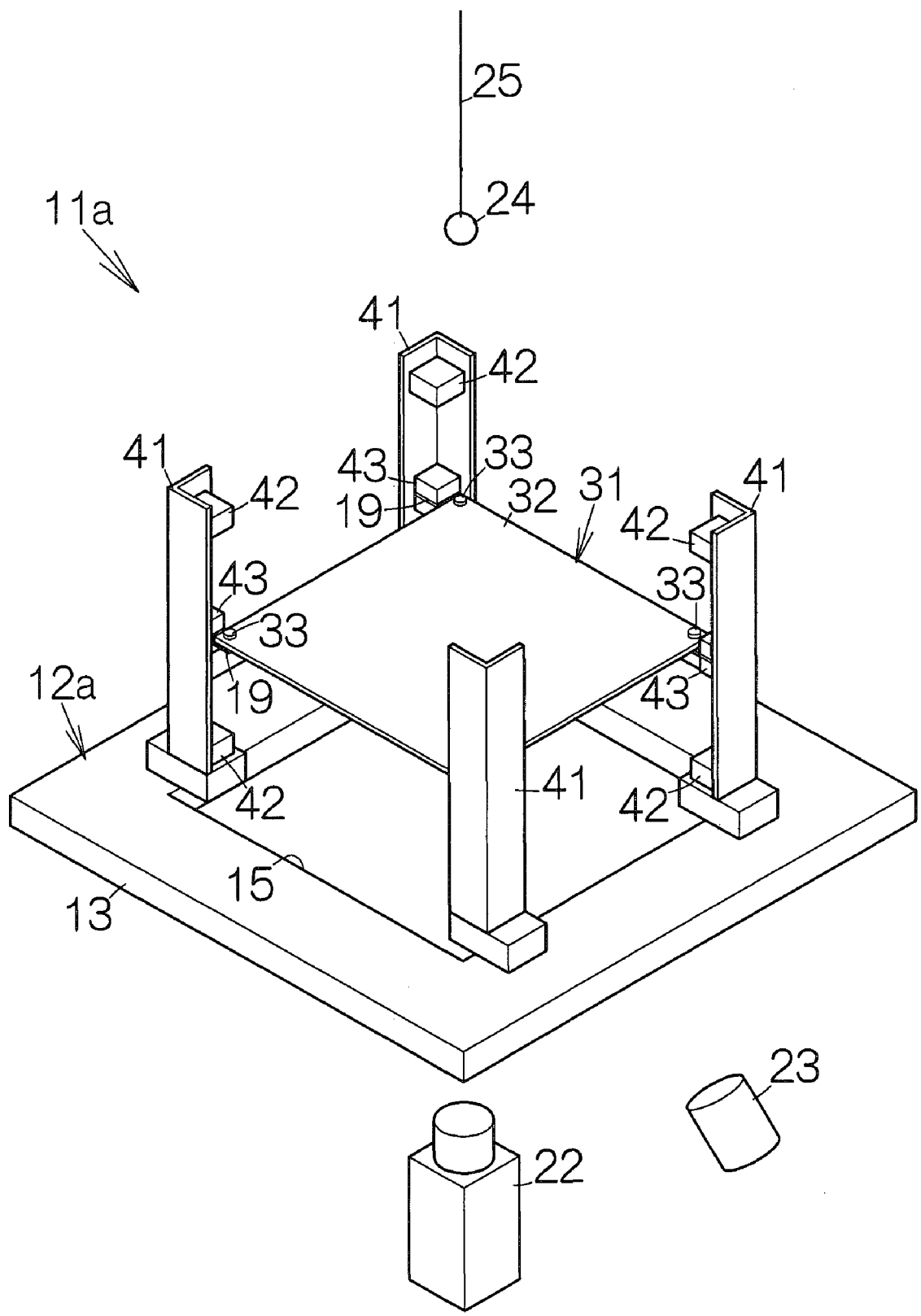
FIG. 5 is a perspective view schematically illustrating the impact test apparatus with a test sample attached.

As shown in FIG. 5, the test sample 31 is attached to the retaining member 19 in an impact test. Screws 33 are employed to attach the test sample 31. The retaining member 19 is supported on the support post 14 with the first and second magnets 42, 43. The allowable distance of relative movement between the test sample 31 and the retaining member 19 is thus set significantly smaller than that of relative movement between the retaining member 19 and the support post 14.

The weight 24 is subjected to a free fall to the upward back surface of the printed wiring board 32 in the same manner as described above. The secondary collision prevention mechanism allows the weight 24 to collide against the back surface of the printed wiring board 32 only once. The test sample 31 is subjected to free oscillation in response to the impact of the collision. Repulsion between the first magnets 42 and the second magnet 43 allows the test sample 31 to move in the vertical direction along the support post 41 along with the retaining member 19. The free oscillation of the test sample 31 is maintained. The repulsion between the first magnets 42 and the second magnet 43 makes the free oscillation damps as time elapses. After a predetermined duration has elapsed, the printed wiring board 32 rests.

The deformation of the LSI package 34 and the printed wiring board 32 is observed based on the image of the moiré fringes captured with the high-speed camera 22 in the same manner as described above. Simultaneously, electric connection is examined between the LSI package 34 and the printed wiring board 32. The bonding strength is in this manner measured between the LSI package 34 and the printed wiring board 32. The impact test apparatus 11a is allowed to enjoy the advantages identical to those obtained in the aforementioned impact test apparatus 11.

The test sample 31 may be soldered to the retaining member 19, for example. The spring coefficient and length of the coil springs 18 and the repulsion between the first and second magnets 42, 43 may depend on the type of the test sample 31. These conditions may correspondingly be adjusted. In addition, the first and second magnets 42, 43 may be an electromagnet in place of a permanent magnet, for example. An electronic apparatus such as a mobile phone terminal may be attached to the test sample 31, for example. Almost the same impact as an actual impact is in this manner applied in the impact test.

What is claimed is:

1. An impact test apparatus comprising:
   a support;
   a first magnet fixed to the support;
   a second magnet supported on the support for relative movement based on a repulsion between the first magnet and the second magnet;
   a retaining member attached to the second magnet so as to retain a test object; and
   a weight made to collide against the test object.

2. The impact test apparatus according to claim 1, wherein an allowable distance of relative movement between the retaining member and the test object is set smaller than an allowable distance of relative movement between the retaining member and the support.

* * * * *